(12) United States Patent
Mercer

(10) Patent No.: US 10,257,330 B1
(45) Date of Patent: Apr. 9, 2019

(54) MOBILE DEVICE WITH AN INTEGRATED HAZARDOUS CONDITION DETECTION SYSTEM

(71) Applicant: Ben Mercer, Kansas City, MO (US)

(72) Inventor: Ben Mercer, Kansas City, MO (US)

(*) Notice: Subject to any disclaimer, the term of this patent is extended or adjusted under 35 U.S.C. 154(b) by 0 days.

(21) Appl. No.: 16/146,321

(22) Filed: Sep. 28, 2018

Related U.S. Application Data

(60) Provisional application No. 62/569,214, filed on Oct. 6, 2017.

(51) Int. Cl.
*H04M 1/02* (2006.01)
*G01N 33/00* (2006.01)
*G01N 27/72* (2006.01)

(52) U.S. Cl.
CPC ....... *H04M 1/0206* (2013.01); *H04M 1/0262* (2013.01); *H04M 1/0264* (2013.01); *G01N 27/72* (2013.01); *G01N 33/0057* (2013.01)

(58) Field of Classification Search
CPC ............. H04M 1/0206; H04M 1/0262; H04M 1/0264; G01N 24/12; G01N 33/0057
USPC ........................................................ 455/575.1
See application file for complete search history.

(56) References Cited

U.S. PATENT DOCUMENTS

| | | | | |
|---|---|---|---|---|
| 2004/0119591 | A1* | 6/2004 | Peeters | G08B 21/0222 340/539.26 |
| 2012/0188940 | A1* | 7/2012 | Agrawal | H04W 4/185 370/328 |
| 2013/0295538 | A1* | 11/2013 | Ambrose | G09B 9/00 434/218 |

* cited by examiner

*Primary Examiner* — Lee Nguyen

(57) ABSTRACT

A mobile device with an integrate hazardous detection system which surveys the surrounding area for potential dangers to the wearer. The system includes a mobile device, a housing body, a plurality of holes, an external microcontroller, and a plurality of hazardous condition detectors. The housing body encloses and protects the electronic components and is mounted adjacent to a rear surface of a main enclosure body of the mobile device. The hazardous condition detectors survey the area for dangerous indicators such as smoke, explosive chemicals, oncoming traffic, and guns to name a few non-limiting examples. The hazardous condition detectors are distributed about the rear surface and mounted within the housing body. The holes expose the hazardous condition detectors to the environment outside the housing body. Specifically, the holes traverse into the housing body. The microcontroller gathers and analyzes the data gathered by the hazardous condition detectors.

8 Claims, 5 Drawing Sheets

MOBILE DEVICE WITH AN INTEGRATED HAZARDOUS CONDITION DETECTION SYSTEM

The current application claims a priority to the U.S. Provisional Patent application Ser. No. 62/569,214 filed on Oct. 6, 2017.

FIELD OF THE INVENTION

The present invention generally relates to a mobile device. More specifically the present invention is a mobile device with an integrated hazardous condition detection system which alerts a user of a variety of immediate dangers. Specifically, the present invention detects ingredients for making a bomb or explosive devices, guns, and smoke.

BACKGROUND OF THE INVENTION

As technology develops and the exchange of information becomes increasingly accessible people look for additional ways of securing their surroundings. Unfortunately, we live in a world where modern day threats can be very difficult to detect in a timely manner. Preventive measures are tough to implement due the unpredictable nature of such horrific events. Saving lives is the ultimate goal, therefore the response times with which rescue authorities are deployed is critical, and directly proportional to the number of people that may potentially be saved. The widespread of internet connectivity allows people to communicate instantly at the touch of a button. As a result, alert systems have been adopted by mobile device manufacturers which allow authorities to send out audible alerts to every mobile device in a specific area, in case of an emergency situation. These alerts are certainly helpful in notifying a person of a possible danger, however usually they are deployed after the event has occurred. Making a phone call, sending a text or a multimedia file are all features that a modern smart phone can accomplish within seconds. Due to the processing power of such devices, numerous other features may be integrated for the convenience and safety of the user.

As security measures are increased in densely populated areas, various methods of prevention may be adapted. Airplanes for example, have become some of the most secured methods of transportation. Thorough security checks are conducted at airports, which are capable of detecting hazardous materials and conditions. People are checked for explosive materials, and weapons before embarking on an airline to prevent any potential disasters. These types of checkpoints require crowd management, and individual examination, therefore they are not suitable for large public events. The present invention aims to solve some of the problems mentioned above, by integrating numerous preventive features into a cell phone.

DETAIL DESCRIPTIONS OF THE INVENTION

All illustrations of the drawings are for the purpose of describing selected versions of the present invention and are not intended to limit the scope of the present invention.

People often look for ways to increase the safety and security of their surroundings. While conventional mobile devices are able to transmit distress signals if necessary they are limited in their ability to detect hazardous situations. The present invention combines the versatility of a smartphone, with additional security features that may help save the life of a user, by detecting potentially hazardous situations or conditions around the user. The present invention may be implemented as a premanufacturing design or an aftermarket upgrade.

Figure 1:
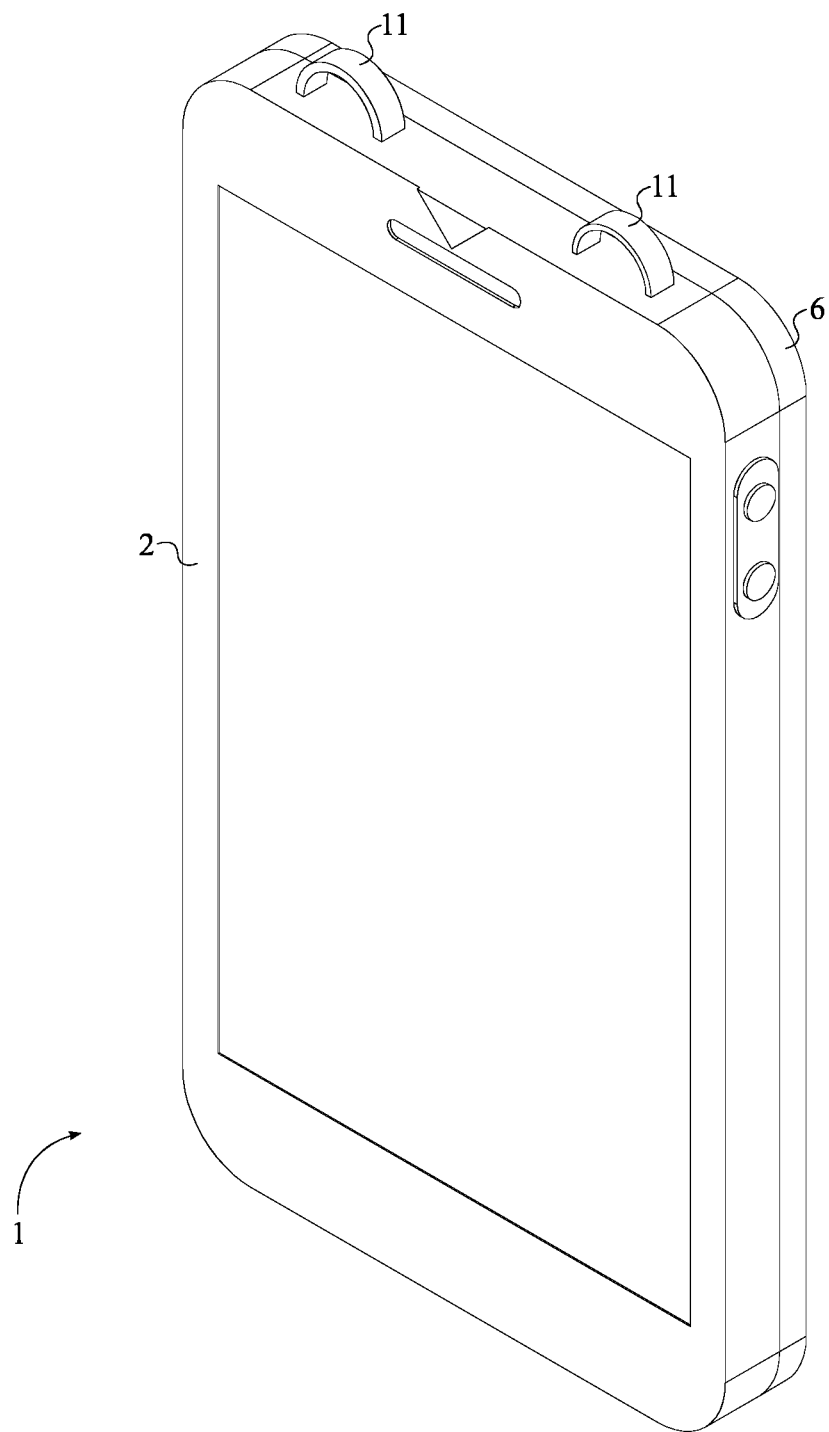
FIG. 1 is a perspective view of the present invention.
Figure 2:
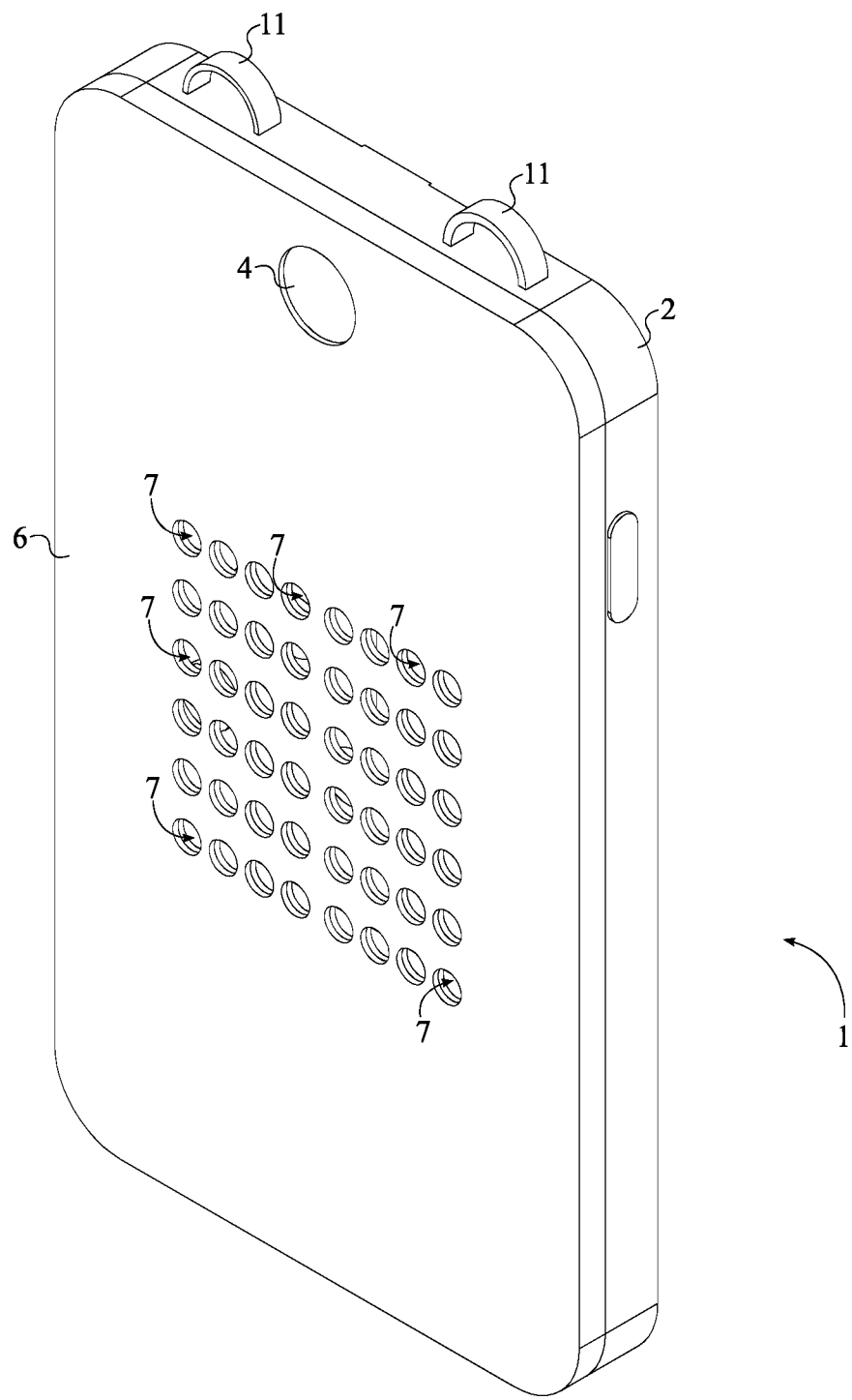
FIG. 2 is a rear perspective view of the present invention.

Referring to FIG. 1 and FIG. 2, the present invention is a mobile device 1 with an integrated hazardous condition detection system. More specifically, the present invention comprises a mobile device 1, a housing body 6, a plurality of holes 7, an external microcontroller 8, and a plurality of hazardous condition detectors 12.

The mobile device 1 is any cell phone, smartphone, or other similar portable computing device. The mobile device 1 comprises a main enclosure body 2, an at least one camera 4, an antenna 5, an internal microcontroller, a speaker, a user interface, a tactile display, an internal battery, and a global positioning system (GPS) module. However, additional features and or components may also be integrated into the mobile device 1. The antenna 5 and the speaker are positioned at a top end of the main enclosure body 2. The information gathered and analyzed by the present invention is transmitted to the user through the user interface and the tactile display. The GPS module allows the present invention to provide search and rescue operations with an accurate location for quick and effective rescue missions. The camera 4 allows for documentation of hazardous materials and situations.

The housing body 6 encloses and protects the plurality of hazardous condition detectors 12 and the supporting components necessary for the functions of the present invention. More specifically, the housing body 6 is a hollow structure that is preferably sized and shaped complimentary to the main enclosure body 2. Essentially, the housing body 6 acts as a secondary backing of the mobile device 1. The housing body 6 is positioned adjacent to a rear surface 3 of the main enclosure body 2 and is mounted adjacent to the rear surface 3 to form an internal compartment. It is preferred that the housing body 6 is shaped and sized complimentary to the rear surface 3 and that the housing body 6 is perimetrically connected to the rear surface 3. The shape, material composition, positioning, and thickness of the housing body 6 is subject to change to fit the needs of various detectors from the plurality of hazardous condition detectors 12.

Referring to FIG. 2, in the preferred embodiment of the present invention, the camera 4 is integrated into the housing body 6 to allow for video and image recording directly behind the mobile device 1, coincident with the orientation of the majority within the plurality of hazardous condition detectors 12. The camera 4 is positioned adjacent to the housing body 6, opposite the main enclosure body 2. Additionally, the camera 4 is integrated into the housing body 6 and is oriented away from the main enclosure body 2. The present invention also utilizes image and video processing software in order to process images and video in real time to identify potentially dangerous items and situations. For this, the external microcontroller 8 is electronically connected to the camera 4 and the mobile device 1. One example is face recognition software, wherein the images recorded by the camera 4 are processed against a database of known criminals, wanted individuals, or other possibly questionable individuals. Any positive identification will be displayed to the user for his or her own safety.

Figure 3:
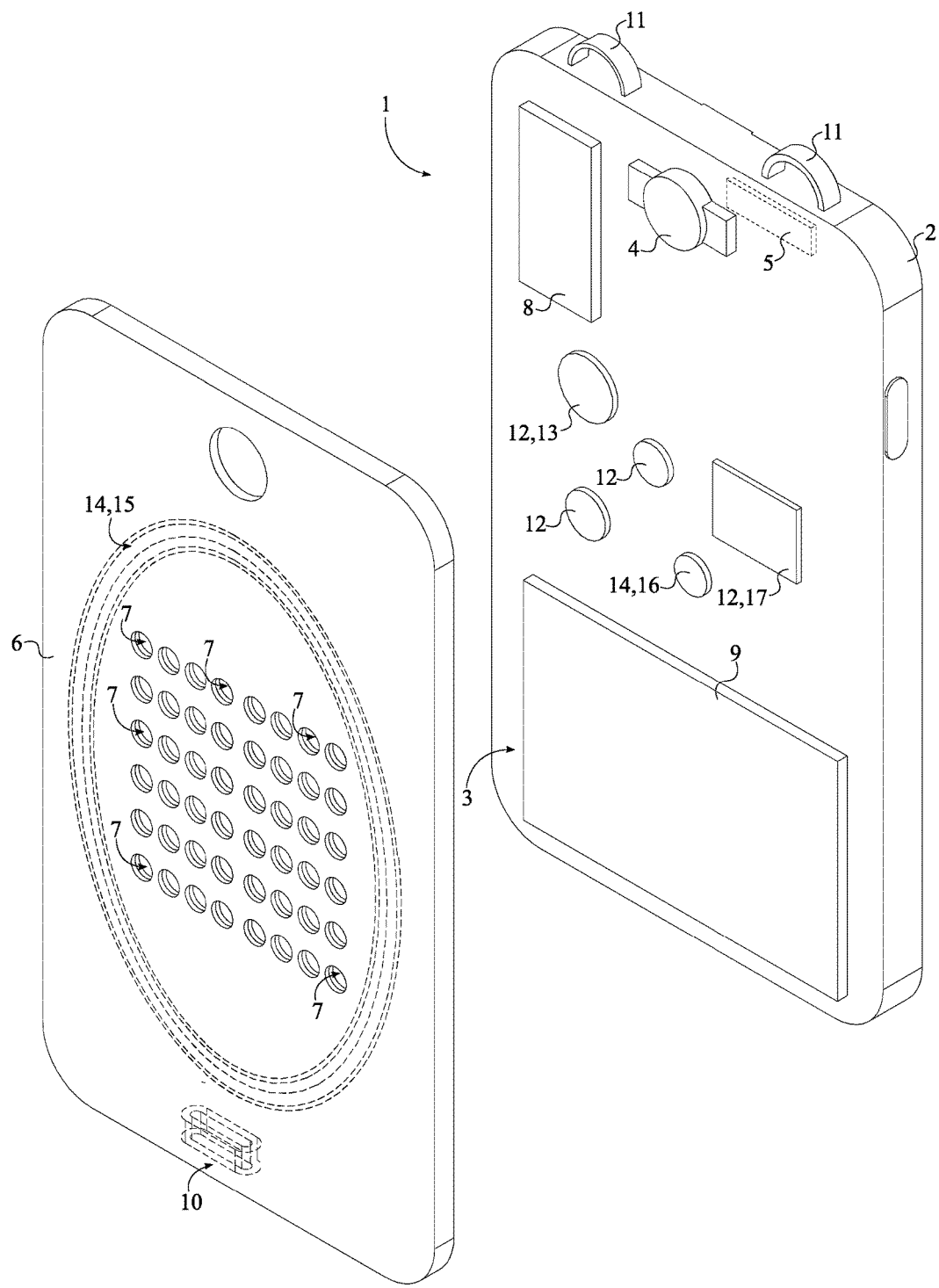
FIG. 3 is a rear perspective view of the present invention in an exploded state.

Each of the plurality of hazardous condition detectors 12 is a device, instrument, or sensor designed to identify a specific factor, environmental agent, or chemical presence which may indicate a dangerous environment for the user. The plurality of hazardous condition detectors 12 is distributed about the rear surface 3 with each of the plurality of hazardous condition detectors 12 being mounted within the housing body 6. The housing body 6 protects the plurality of hazardous condition detectors 12 from physical damage to ensure product longevity and accurate data collection without external interference. The plurality of holes 7 exposes an at least one from the plurality of hazardous condition detectors 12 to the environment directly surrounding the housing body 6. The plurality of holes 7 is distributed across the housing body 6, opposite to the main enclosure body 2. Referring to FIG. 3, each of the plurality of holes 7 normally traverses into the housing body 6, opposite the main enclosure body 2. As such, the internal compartment is configured to be in fluid communication with the surrounding environment. This allows the present invention to evaluate the surrounding environment based on preset criteria and data gathered by the plurality of hazardous condition detectors 12. The size, shape, number, and position of each of the plurality of holes 7 is subject to change to correspond to the exposure needs for the plurality of hazardous condition detectors 12.

Figure 5:
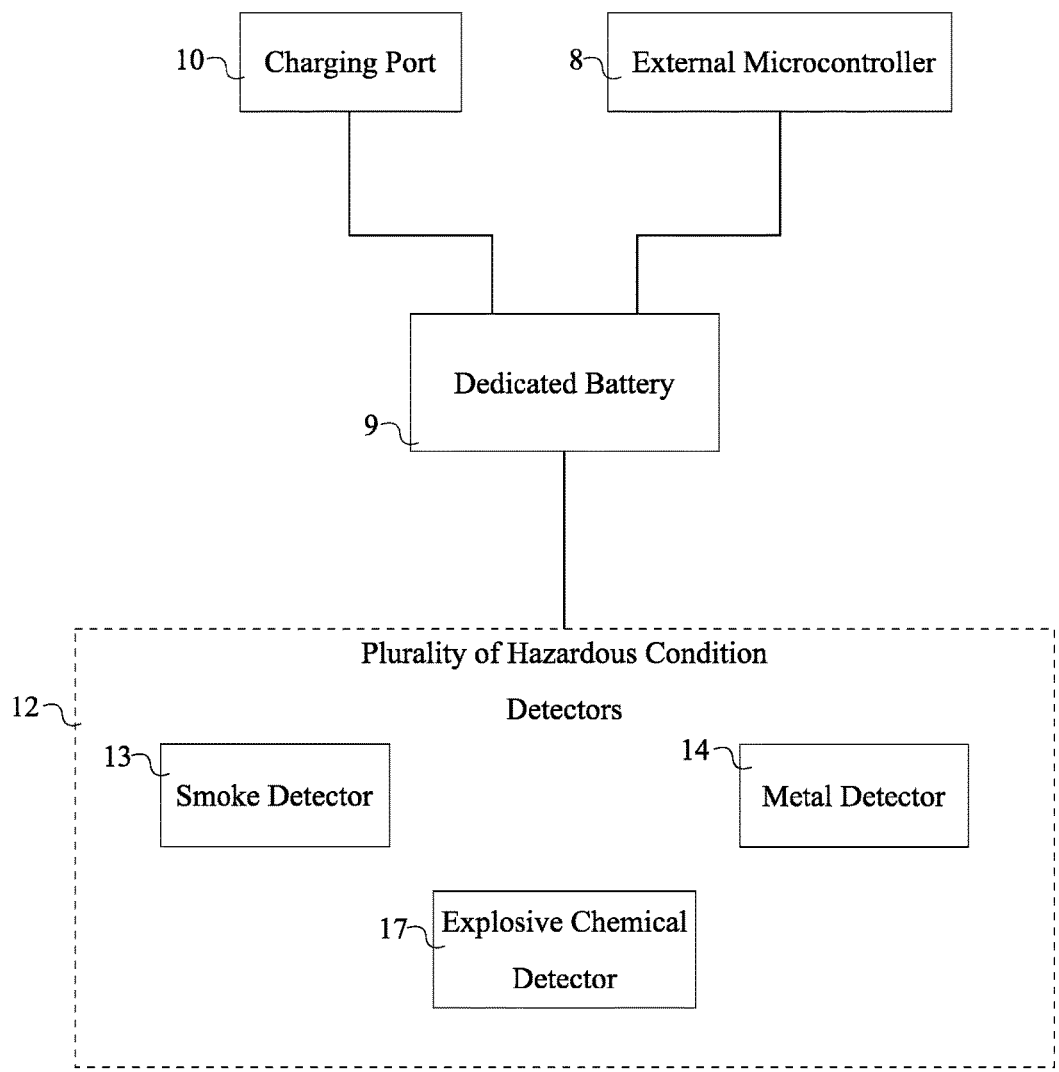
FIG. 5 is an electric schematic diagram of the present invention.

The information and data recorded by the plurality of hazardous condition detectors 12 is received and analyzed by the external microcontroller 8. The need for the external microcontroller 8 is to allow the present invention to work regardless of the mobile device 1 being turned on or off. As such, the present invention protects the user at all times. The external microcontroller 8 is mounted within the housing body 6 and is electronically connected to each of the plurality of hazardous condition detectors 12. For this, the present invention further comprises a dedicated battery 9 and a charging port 10. The dedicated battery 9 provides the necessary electricity to power the present invention and the charging port 10 allows the user to recharge the dedicated battery 9. Specifically, the dedicated battery 9 is mounted within the housing body 6, adjacent to the rear surface 3 so as not to obstruct the plurality of hazardous condition detectors 12. In one embodiment, the dedicated battery 9 is removable for quick and efficient charging. Additionally, referring to FIG. 5, the dedicated battery 9 is electrically connected to the external microcontroller 8, each of the plurality of hazardous condition detectors 12, and the charging port 10. The charging port 10 allows for the dedicated battery 9 to be recharged by an external power supply and is thus laterally integrated into the housing body 6. In alternative embodiment, the external microcontroller 8 and the plurality of hazardous condition detectors 12 may be powered by either and or both the dedicated battery 9 or the internal battery. Similarly, the data collected by the plurality of hazardous condition detectors 12 may be analyzed by either and or both the internal microcontroller and the external microcontroller 8.

Figure 4:
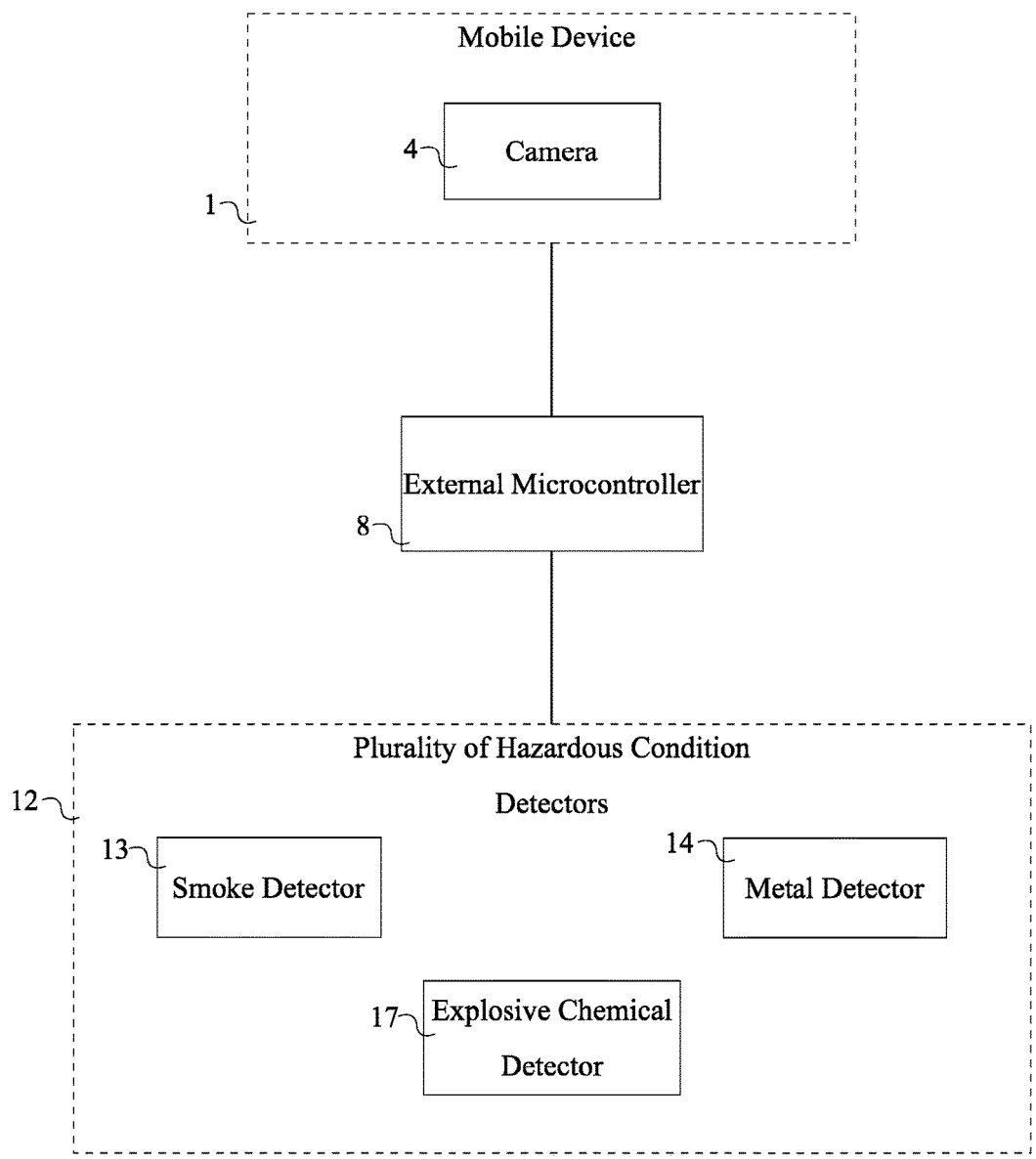
FIG. 4 is an electronic schematic diagram of the present invention.

Referring to FIG. 3 and FIG. 4, the plurality of hazardous condition detectors 12 comprises at least the following: a smoke detector 13, a metal detector 14, and an explosive chemical detector 17. The smoke detector 13 senses smoke around the mobile device 1, indicating a fire in close vicinity of the user. For the smoke detector 13 to function properly, the smoke detector 13 is positioned adjacent to a corresponding hole from the plurality of holes 7. In one embodiment of the present invention, the smoke detector 13 utilizes a physical process, ionization, in order to detect smoke. In another embodiment of the present invention, the smoke detector 13 senses smoke optically. If smoke is identified by the smoke detector 13, then the present invention is put into an emergency state. In the emergency state, the present invention emits an alert, preferably through the mobile device 1. The alert may include a tactile vibration, a visual alert notification, and or an audible alert notification.

The metal detector 14 identifies nearby metallic items. This is used to notify the user of potential weapons, specifically guns, that may be present in the vicinity. In one embodiment, the metal detector 14 is implemented as a standard design, wherein the metal detector 14 comprises a search head coil 15 and a magnemeter 16. The search head coil 15 is a wire configured in a spiral or circular fashion. An alternating current is passed through the search head coil 15 in order to produce an alternating magnetic field. If a metallic item is positioned close to the search head coil 15, then eddy currents will be created within the metallic item and an additional magnetic field will be produced by the metallic item. Referring to FIG. 3, the search head coil 15 is positioned parallel to the rear surface 3 and is integrated into the housing body 6. The magnemeter 16 is a sensor which measures magnetism and is used to detect the additional magnetic field created by the metallic item, thus indicating the presence of metal nearby. As such, the magnemeter 16 is mounted within the housing body 6. The dedicated battery 9 is electrically connected to the search head coil 15 and the magnemeter 16. Additionally, the external microcontroller 8 is electronically connected to the search head coil 15 and the magnemeter 16. If a metallic item of specific structure is identified by the metal detector 14, then the present invention is put into the emergency state; wherein the specific structure is preset and predetermined to correlate with the structure of a gun or other metallic weapons.

In another embodiment of the present invention, the metal detector 14 detects electromagnetic waves emitted by a person to identify potential gun profiles on said person. Specifically, in this embodiment, the metal detector 14 detects electromagnetic waves with a frequency in the terahertz range. Human bodies emit these types of waves, similar to infrared radiation, but terahertz waves do not pass through conductive material. Resultantly, scanning a region for terahertz waves will produce missing patches or outlines if there is a metallic object is present. The metal detector 14 produces images of the scanned regions directly around the mobile device 1 and the external microcontroller 8 process these images in real time to search for guns and other potentially dangerous items based on preset criteria, image outline, and other similar characteristics. In another embodiment of the present invention, the metal detector 14 emits radio waves in order to survey, or image, the area directly around the mobile device 1. The metal detector 14 and the external microcontroller 8 analyze the reflection pattern of the emitted radio waves to identify potential guns in the nearby vicinity. Additionally, this method may also be used to identify other dangerous items around the mobile device 1. If a dangerous item is identified, then the present invention is put into the emergency state in order to notify the user.

The explosive chemical detector 17 detects various explosive materials that are commonly used in bombs such as nitroglycerine, nitro methane, hydrogen peroxide, and pan cordite to name a few non-limiting examples. A variety of mechanisms and sensors may be used as the explosive chemical detector 17.

Referring to FIG. 1, the present invention further comprises an at least one strap-attachment loop 11. The strap-attachment loop 11 is a semi-annular structure that allows the user to attach the present invention to an external structure such as a necklace or a strap. The strap-attachment loop 11 is positioned adjacent to the antenna 5 such that when the present invention is worn around the neck, the antenna 5 is elevated, and the present invention is vertically oriented for better reception. The strap-attachment loop 11 is laterally and externally connected to the main enclosure body 2. In the preferred embodiment of the present invention, referring to FIG. 1, the at least one strap-attachment loop 11 comprises a first loop and a second loop. The first loop and the second loop are positioned offset to each other to provide a single strap two attachment points to the present invention.

In alternative embodiments of the present invention, the plurality of hazardous condition detectors 12 is selected from the group consisting of an electromagnetic radiation detector, a microphone, a motion detector, an infrared sensor, a magnetic sensor, a temperature sensor, a humidity sensor, and a gas sensor. The electromagnetic radiation detector may be used to identify potentially high radiation levels near the user. The microphone may be used to scan conversations directly around the user for trigger words/sentences that may be associated with dangerous activities. The motion detector may be used to detect oncoming traffic on a collision course with the user. The temperature sensor and the humidity sensor may be used to identify dangerous weather and environment conditions. The gas sensor may be used to identify gas leaks and other similar dangerous chemicals.

Once the present invention detects an imminent danger, the normal cell phone functionality is stopped for the mobile device 1, and the user is alerted on the tactile display, via a visual and audible alert that is immediately distinguishable from the normal alerts. The alert signal immediately activates the camera 4 documenting and storing the data collected during the incident. The specific response of the present invention to detection of a hazardous condition may be altered by the user to meet his or her needs and preferences.

In alternative embodiments, the present invention may also comprise an external speaker and an external flash that are mounted to the housing body 6. The external speaker and the external flash provide additional means for notifying the user about a potential dangerous situation.

Although the invention has been explained in relation to its preferred embodiment, it is to be understood that many other possible modifications and variations can be made without departing from the spirit and scope of the invention as hereinafter claimed.

What is claimed is:

1. A mobile device with an integrated hazardous condition detection system comprises:
    a mobile device;
    a housing body;
    a plurality of holes;
    an external microcontroller;
    a plurality of hazardous condition detectors;
    the mobile device comprises a main enclosure body;
    the housing body being positioned adjacent to a rear surface of the main enclosure body;
    the housing body being adjacently mounted to the rear surface;
    the plurality of hazardous condition detectors being distributed about the rear surface;
    each of the plurality of hazardous condition detectors being mounted within the housing body;
    each of the plurality of holes normally traversing through the housing body, opposite to the main enclosure body;
    the external microcontroller being mounted within the housing body; and
    the external microcontroller being electronically connected to each of the plurality of hazardous condition detectors.

2. The mobile device with an integrated hazardous condition detection system as claimed in claim 1 comprises:
    the mobile device further comprises an at least one camera;
    the camera being positioned adjacent to the housing body, opposite the main enclosure body;
    the camera being integrated into the housing body;
    the camera being oriented away from the main enclosure body; and
    the external microcontroller being electronically connected to the camera.

3. The mobile device with an integrated hazardous condition detection system as claimed in claim 1 comprises:
    a dedicated battery;
    a charging port;
    the dedicated battery being mounted within the housing body, adjacent to the rear surface;
    the charging port being laterally integrated into the housing body; and
    the dedicated battery being electrically connected to the external microcontroller, the charging port, and the plurality of hazardous condition detectors.

4. The mobile device with an integrated hazardous condition detection system as claimed in claim 1 comprises:
    the mobile device further comprises an antenna;
    an at least one strap-attachment loop;
    the strap-attachment loop being positioned adjacent to the antenna; and
    the strap-attachment loop being laterally and externally connected to the main enclosure body.

5. The mobile device with an integrated hazardous condition detection system as claimed in claim 1 comprises:
    the plurality of hazardous condition detectors comprises a smoke detector; and
    the smoke detector being positioned adjacent to a corresponding hole from the plurality of holes.

6. The mobile device with an integrated hazardous condition detection system as claimed in claim 1 comprises:
    the plurality of hazardous condition detectors comprises a metal detector;
    the metal detector comprises a search head coil and a magnemeter;
    the search head coil being positioned parallel to the rear surface;
    the search head coil being integrated into the housing body;
    the magnemeter being mounted within the housing body; and
    the external microcontroller being electronically connected to the search head coil and the magnemeter.

7. The mobile device with an integrated hazardous condition detection system as claimed in claim 1, wherein the plurality of hazardous condition detectors comprises an explosive chemical detector.

8. The mobile device with an integrated hazardous condition detection system as claimed in claim 1, wherein the plurality of hazardous condition detectors is selected from the group consisting of an electromagnetic radiation detector, a microphone, a motion detector, an infrared sensor, a magnetic sensor, a temperature sensor, a humidity sensor, and a gas sensor.

* * * * *